United States Patent
Ren et al.

(10) Patent No.: US 12,122,804 B2
(45) Date of Patent: Oct. 22, 2024

(54) γ-AMINOBUTYRIC ACID MODULATOR CRYSTAL FORM X, PREPARATION METHOD AND APPLICATION THEREOF

(71) Applicant: SHENZHEN RENTAI PHARMATECH LTD., Guangdong (CN)

(72) Inventors: Guobin Ren, Shenzhen (CN); Weijie Ji, Shenzhen (CN); Dongxu Yi, Shenzhen (CN); Jiajun Huang, Shenzhen (CN)

(73) Assignee: SHENZHEN RENTAI PHARMATECH LTD., Guangdong (CN)

( * ) Notice: Subject to any disclaimer, the term of this patent is extended or adjusted under 35 U.S.C. 154(b) by 749 days.

(21) Appl. No.: 17/426,951

(22) PCT Filed: Jan. 31, 2019

(86) PCT No.: PCT/CN2019/074272
§ 371 (c)(1),
(2) Date: Jul. 29, 2021

(87) PCT Pub. No.: WO2020/155057
PCT Pub. Date: Aug. 6, 2020

(65) Prior Publication Data
US 2022/0098230 A1 Mar. 31, 2022

(51) Int. Cl.
*C07J 7/00* (2006.01)
*C07J 43/00* (2006.01)
(52) U.S. Cl.
CPC ........... *C07J 7/009* (2013.01); *C07B 2200/13* (2013.01); *C07J 43/003* (2013.01)

(58) Field of Classification Search
CPC .............. A61K 31/415; C07B 2200/13; C07D 231/14; C07J 43/003; C07J 7/009; A61P 25/00
See application file for complete search history.

(56) References Cited

U.S. PATENT DOCUMENTS 10,172,871 B2    1/2019   Martinez Botella et al.

FOREIGN PATENT DOCUMENTS

| CN | 105339381 A | 2/2016 |
| WO | 2018039378 A1 | 3/2018 |

OTHER PUBLICATIONS

China National Intellectual Property Administration (CNIPA); Second Office Action of Corresponding Application No. 2019800036610 with English translation; Date of Notification: Mar. 9, 2022; pp. 1-5.
Notification of First Office Action of corresponding CN Application No. 2019800036610; China National Intellectual Property Administration; Mail Date: Jul. 26, 2021; pp. 1-8.
China National Intellectual Property Administration, Written Opinion of the International Searching Authority for PCT/CN2019/074272; Mail Date: Oct. 31, 2019; pp. 1-7.
(Continued)

*Primary Examiner* — Sarah Pihonak
*Assistant Examiner* — Padmaja S Rao
(74) *Attorney, Agent, or Firm* — Taft Stettinius & Hollister LLP; Stephen F. Rost (57) ABSTRACT

A crystal form X of 3α-hydroxy-3β-methyl-21-(4-cyano-1H-pyrazol-1'-yl)-19-nor-5β-pregnan-20-one, a preparation method of said crystal form and an application thereof in preparing a drug for treatment of central nervous system disease.

20 Claims, 9 Drawing Sheets

(56) References Cited

OTHER PUBLICATIONS

China National Intellectual Property Administration, International Search Report of the International Searching Authority for PCT/CN2019/074272; Mail Date: Oct. 31, 2019; pp. 1-3.
Botella, G.M. et al., "A Clinical Next Generation Neuroactive Steroid Positive Allosteric Modulator of the (γ-Aminobutyric Acid) A Receptor"; Journal of Medicinal Chemistry, vol. 60, 28, Jul. 28, 2017, pp. 7810-7819 (1 Page of relevant excerpt in English).
China National Intellectual Property Administration (CNIPA); Decision of Refusal of Corresponding Application No. 2019800036610 with English translation; Date of Notification: Jun. 6, 2022; pp. 1-4.

γ-AMINOBUTYRIC ACID MODULATOR CRYSTAL FORM X, PREPARATION METHOD AND APPLICATION THEREOF

This application is a U.S. national stage application under 35 U.S.C. § 371 of PCT International Application Serial No. PCT/CN2019/074272, which has an international filing date of Jan. 31, 2019, designates the United States of America, the disclosure of which is hereby expressly incorporated by reference in its entirety.

TECHNICAL FIELD

The present invention belongs to the technical field of preparation of a crystal form, and particularly relates to γ-aminobutyric acid modulator crystal form X, preparation method and application thereof.

BACKGROUND

There are nearly 500 million patients with various central nervous system-related diseases worldwide, and there are 170 million patients in China alone. Mental illness is not only an individual problem, but also a public health problem and a social problem, which has received increasing attention from the state. It is known that mental illness ranks first in the total burden of disease in China, surpassing diseases such as cardiovascular and cerebrovascular diseases, respiratory system, and malignant tumors. However, the current medicaments for treating mental illness are far from meeting people's relevant clinical needs, and new medicaments need to be continuously developed.

3α-hydroxy-3β-methyl-21-(4-cyano-1H-pyrazol-1'-yl)-19-nor-5β-pregnan-20-one, also known as Sage217, is a new type of neuroactive steroid γ-aminobutyric acid modulator, which is developed by Sage Therapeutics Co., Ltd. (SAGE, US) and used as a medicament for preventing and treating various central nervous system (CNS) related diseases, such as sleep disorder, mood disorder, schizophrenia spectrum disorder, spasticity disorder, memory disorder and/or cognitive disorder, dyskinesia, personality disorder, autism spectrum disorder, pain, traumatic brain injury, vascular disease, substance abuse disorder and/or withdrawal syndrome or tinnitus, and is especially effective for major depression and postpartum depression. Sage-217 has a structural formula as follows:

Patent application WO2018039378A1 filed by SAGE company discloses a total of 16 crystal forms including crystal forms A, B, C, D, E, F, C, D, E, F, G, H, I, J, K, L, M, N, O, and P. Wherein, the crystal forms A, C and K are anhydrous stable crystal forms, and the crystal forms B, F, L, M, N, O, and P are solvated crystal forms. Considering solubility toxicity, the latters are not suitable for medicinal form. Crystal forms D, E, H, I, and J are metastable crystal forms, which will undergo crystal transformation after being used as a medicament, and the product quality cannot be controlled homogeneously. In addition, crystal form A will transform to crystal forms C and K, wherein crystal form C contains more solvents (with a weight loss of close to 4.28%) and will transform to crystal form K (FIG. 3G), so both crystal form A and crystal form C are unstable, and are not suitable for medicinal crystal form. Meanwhile, the characteristic peaks, especially at 2θ of 10°, of the crystal form K are inconsistent under different temperature conditions, indicating that the crystal form K is unstable and is easy to transform, or it is a mixed crystal, and thus not suitable to be used as a medicinal crystal form.

Different crystal forms of solid chemical drugs can cause differences in their solubility and stability, thereby affecting the absorption and bioavailability of the drugs, and leading to differences in clinical efficacy. Inventors of the present application have developed a crystal form X of Sage-217 through a large number of experimental studies, providing a new and better choice for the preparation of pharmaceutical preparations comprising Sage-217, and having great significance for drug development.

SUMMARY OF THE INVENTION

Therefore, in order to overcome the technical problems that crystal forms in the prior art are not suitable for use as medicinal crystal forms because they are either unstable or contain large amounts of solvents, in one aspect the present invention provides a new crystal form of 3α-hydroxy-3β-methyl-21-(4-cyano-1H-pyrazol-1'-yl)-19-nor-5β-pregnan-20-one, namely a crystal form X of the γ-aminobutyric acid modifier, and in other aspect the present invention also provides a preparation method and application of the crystal form X.

In one aspect, the present invention provides a crystal form X of γ-aminobutyric acid modulator, wherein, the γ-aminobutyric acid modulator is 3α-hydroxy-3β-methyl-21-(4-cyano-1H-pyrazol-1'-yl)-19-nor-5β-pregnan-20-one, and the crystal form X has characteristic peaks at 2θ diffraction angles of 9.582°±0.2°, 9.916°±0.2°, 11.638°±0.2° 13.399°±0.2° 13.861°±0.2° 16.739°±0.2° 18.661°±0.2° 19.198°±0.2°, 19.919°±0.2°, 20.78°±0.2°, 21.217°±0.2°, 21.943°±0.2°, 23.082°±0.2° and 23.437°±0.2° in X-ray powder diffraction pattern.

Preferably, the crystal form X has further characteristic peaks at 2θ diffraction angles of 24.96°±0.2°, 26.157°±0.2°, 26.539°±0.2° and 27.439°±0.2° in X-ray powder diffraction pattern.

Preferably, the crystal form X has following characteristic peaks in X-ray powder diffraction pattern:

| No. of Peaks | 2θ (°) | Relative intensity (%) |
|---|---|---|
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |

-continued

| No. of Peaks | 2θ (°) | Relative intensity (%) |
|---|---|---|
| 13 | 23.082 | 38.7 |
| 14 | 23.437 | 20.2 |

More preferably, the crystal form X has following characteristic peaks in X-ray powder diffraction pattern:

| No. of Peaks | 2θ (°) | Relative intensity (%) |
|---|---|---|
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |
| 13 | 23.082 | 38.7 |
| 14 | 23.437 | 20.2 |
| 15 | 24.96 | 5 |
| 16 | 26.157 | 7.9 |
| 17 | 26.539 | 8.7 |
| 18 | 27.439 | 7.7 |

More preferably, the crystal form X has following characteristic peaks in X-ray powder diffraction pattern:

| No. | 2θ (°) | Relative intensity (%) |
|---|---|---|
| 1 | 6.885 | 1.7 |
| 2 | 9.582 | 10.5 |
| 3 | 9.916 | 5.2 |
| 4 | 11.638 | 72.9 |
| 5 | 13.399 | 26.1 |
| 6 | 13.861 | 54.3 |
| 7 | 16.739 | 100 |
| 8 | 18.661 | 17 |
| 9 | 19.198 | 49.9 |
| 10 | 19.919 | 18.4 |
| 11 | 20.78 | 14.9 |
| 12 | 21.217 | 12.9 |
| 13 | 21.943 | 24.4 |
| 14 | 23.082 | 38.7 |
| 15 | 23.437 | 20.2 |
| 16 | 24.96 | 5 |
| 17 | 26.157 | 7.9 |
| 18 | 26.539 | 8.7 |
| 19 | 27.439 | 7.7 |

Figure 7:
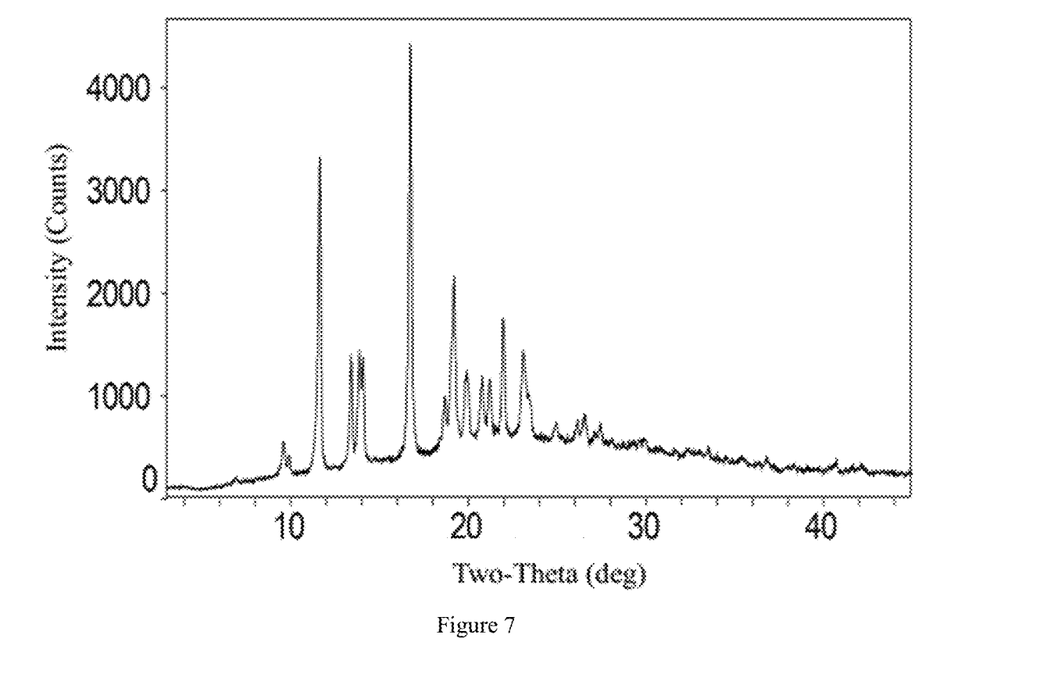
FIG. 7 shows an XRPD pattern of crystal form X in embodiment 5 of the present invention.

More preferably, the crystal form X has a X-ray powder diffraction (XRPD) pattern substantially as shown in FIG. 7.

Preferably, the crystal form X has a characteristic absorption peak at 212.9±2° C. in differential scanning calorimetry (DSC) curve.

Figure 9:
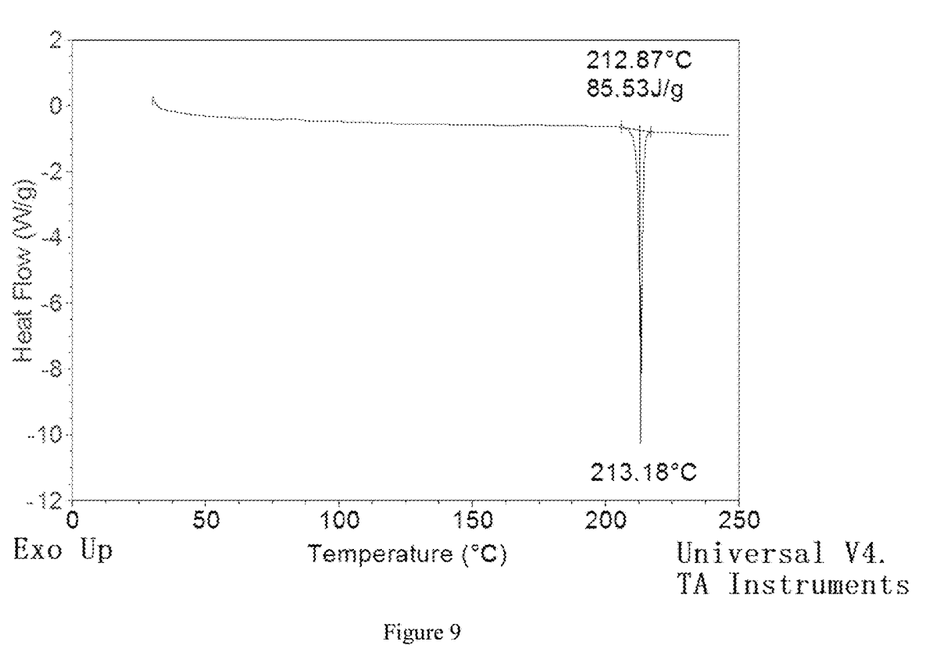
FIG. 9 shows a DSC curve of crystal form X in embodiment 5 of the present invention.

Preferably, the crystal form X has a differential scanning calorimetry (DSC) curve substantially as shown in FIG. 9.

Preferably, the crystal form X has a weight loss of 0.03% before a temperature of 200° C. in thermal gravimetric analysis (TGA) curve.

Figure 10:
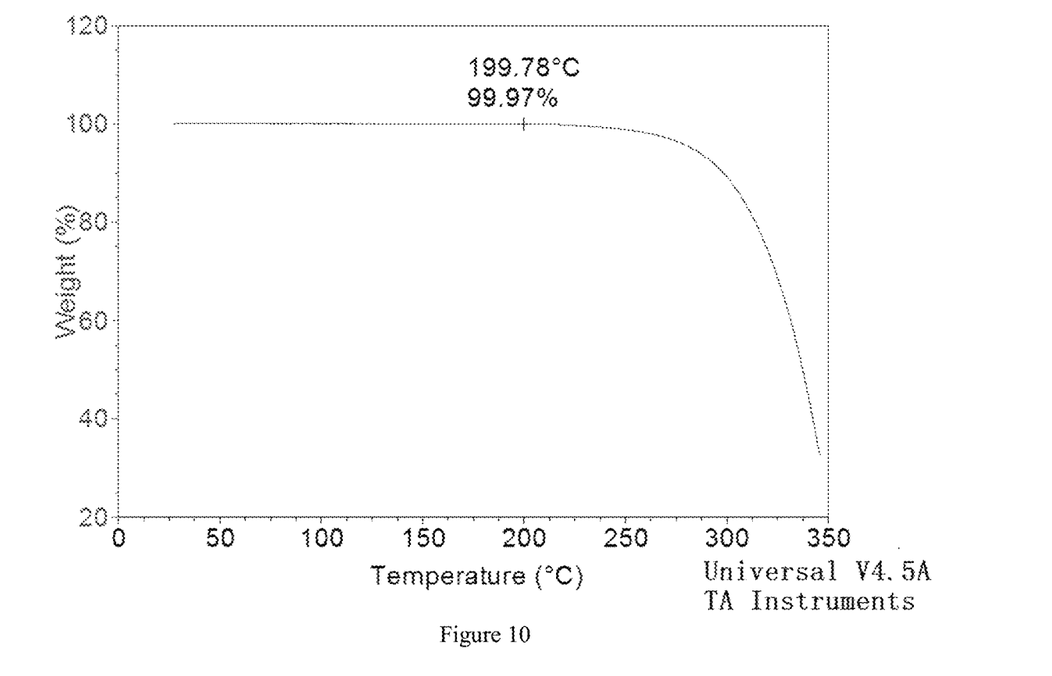
FIG. 10 shows a TGA curve of crystal form X in embodiment 5 of the present invention.

Preferably, the crystal form X has a thermal gravimetric analysis (TGA) curve substantially as shown in FIG. 10.

In another aspect, the present invention provides a method for preparing the above mentioned crystal form X, comprising the following steps:

adding a proper amount of water into a crystal form K to suspend the crystal form K in water at a temperature of 40° C. to 80° C. for 20 h to 25 h to obtain a suspension, filtering the suspension and drying the filter cake to obtain a white solid which is a crystal form X.

Preferably, a ratio of the crystal form K to water is (40 to 60) mg:(1 to 2) mL.

In another aspect, the present invention provides a method for preparing the above mentioned crystal form X, comprising the following steps:

placing a crystal form K in an environment having a humidity of 75% RH to 92.5% RH and a temperature of 25° C. to 40° C. for 3 days to 7 days to obtain a white powder which is a crystal form X.

In another aspect, the present invention provides a pharmaceutical composition, comprising any one of the above-mentioned crystal form X of γ-aminobutyric acid modifier and a pharmaceutically acceptable excipient.

In another aspect, the present invention provides use of any one of the above-mentioned crystal form X, or a crystal form X prepared by any one of the above-mentioned methods, or the above-mentioned pharmaceutical composition in the preparation of a medicament for treating central nervous system diseases.

Preferably in the above use, the central nervous system diseases comprise sleep disorder, mood disorder, schizophrenia spectrum disorder, spasticity disorder, memory disorder and/or cognitive disorder, dyskinesia, personality disorder, autism spectrum disorder, pain, traumatic brain injury, vascular disease, substance abuse disorder and/or withdrawal syndrome or tinnitus.

Preferably in the above use, the medicament is administered orally, parenterally, intradermally, intrathecally, intramuscularly, subcutaneously, vaginally, buccally, sublingually, rectally, topically, by inhalation, intranasally or transdermally.

In another aspect, the present invention provides a method for treating sleep disorder, mood disorder, schizophrenia spectrum disorder, spasticity disorder, memory disorder and/or cognitive disorder, dyskinesia, personality disorder, autism spectrum disorder, pain, traumatic brain injury, vascular disease, substance abuse disorder and/or withdrawal syndrome or tinnitus, comprising a step of administering a pharmaceutically effective amount of the above mentioned pharmaceutical composition to a subject.

The present invention provides a crystal form X of 3α-hydroxy-3β-methyl-21-(4-cyano-1H-pyrazol-1'-yl)-19-nor-5β-pregnan-20-one. This crystal form X has good light stability, high temperature stability, accelerated stability and high humidity stability, and the amount of water or other solvents in this crystal form X is as low as 0.03%, which overcomes the technical problem that crystal forms in the prior art are not suitable for use as medicinal crystal forms because they are unstable or contain high content of solvents content.

BRIEF DESCRIPTION OF THE DRAWINGS

In order to more clearly describe the specific embodiments of the present invention or the technical solutions in the prior art, drawings used in the specific embodiments or the description of the prior art will be briefly introduced as follows. Obviously, the drawings in the following description are some embodiments of the present invention, and other drawings can be obtained according to these drawings without paying creative labor for those skilled in the art.

DETAILED DESCRIPTION OF EMBODIMENTS

The term "bulk pharmaceutical chemical" used in the following embodiments of the present invention refers to crystal form A of 3α-hydroxy-3β-methyl-21-(4-cyano-1H-pyrazol-1'-yl)-19-nor-5β-pregnan-20-one, with a chemical purity of greater than 98%, provided by Shanghai Haoyuan Biomedical Technology Co., Ltd.

Following experimental equipment and test conditions are used in the present application:

X-Ray Powder Diffractometer XRPD
 Model: Uitima IV (Rigaku, Japan)
 Method: Cu target Ka, voltage: 40 KV, current: 40 mA, test angle: 3-45°, scanning step: 0.02, slit width of light pipe: 2 mm, Dtex detector.

X-Ray Single Crystal Diffractometer SXRD
 Model: BRUKER D8 QUEST (BRUKER, Germany)
 Method: Cu target, voltage: 40 KV, current: 30 mA Differential Scanning Calorimeter DSC
 Model: TA 2000 (TA Instruments, US)
 Method: heating at a rate of 10° C./min.

Thermal Gravimetric Analysis TGA
 Model: TA 500 (TA Instruments, US);
 Method: heating at a rate of 10° C./min.

Dynamic Vapor Sorption DVS
 Model: DVS intrinsic (SMS, British);
 Method: 25° C., 10% humidity per step, the judgment standard is less than 0.002% for 10 minutes.

Incubator Light
 Model: TES-1330A (TES Electronic Corp.)

Ultrasound Equipment
 Model: SK8200LHC (Shanghai Kedao Ultrasonic Instrument Co., Ltd.)

Programmable Temperature and Humidity Chamber for Drug Stability
 Model: CMA-100C (Shanghai Puhan Precision Equipment Co., Ltd.)

Figure 1:
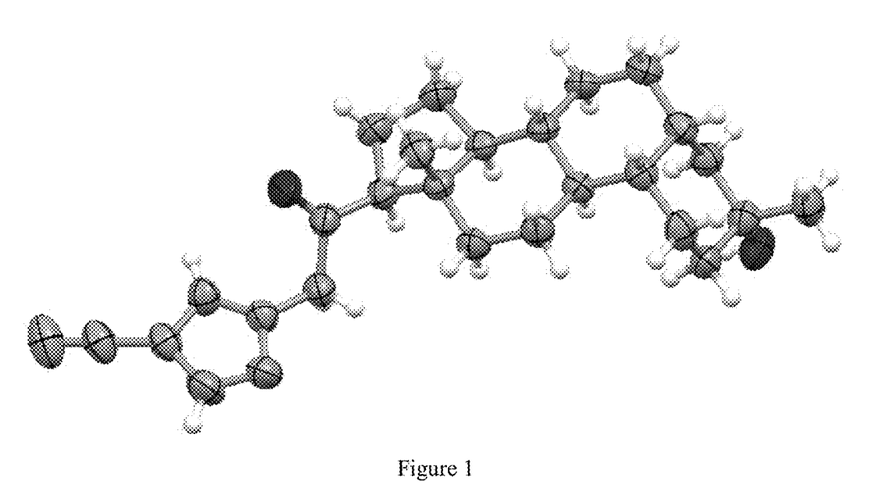
FIG. 1 shows a molecular ellipsoid diagram of single crystal structure of crystal form A in embodiment 1 of the present invention.

Embodiment 1 Analysis of Bulk Pharmaceutical Chemical Crystal Form A 46.2 mg of bulk pharmaceutical chemical is added into a sample vial, and dissolved with 1 mL N,N-dimethylformamide to produce a clear solution. The clear solution is allowed to undergo slow evaporation for 20 days, thus obtaining a single crystal of crystal form A. The obtained single crystal is analyzed with an X-ray single crystal diffractometer, and the obtained data is analyzed by crystallographic structural analysis, and the results are shown in table 1. Molecular ellipsoid diagram of the single crystal structure is shown in FIG. 1.

Figure 2:
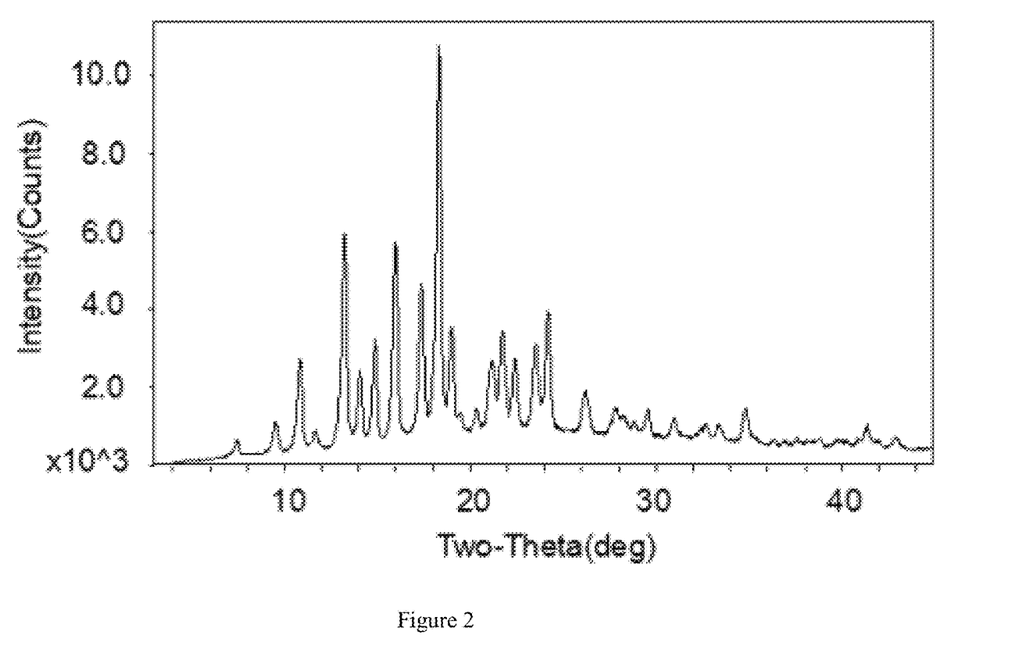
FIG. 2 shows an X-ray power diffraction pattern of crystal form A in embodiment 1 of the present invention.
Figure 3:
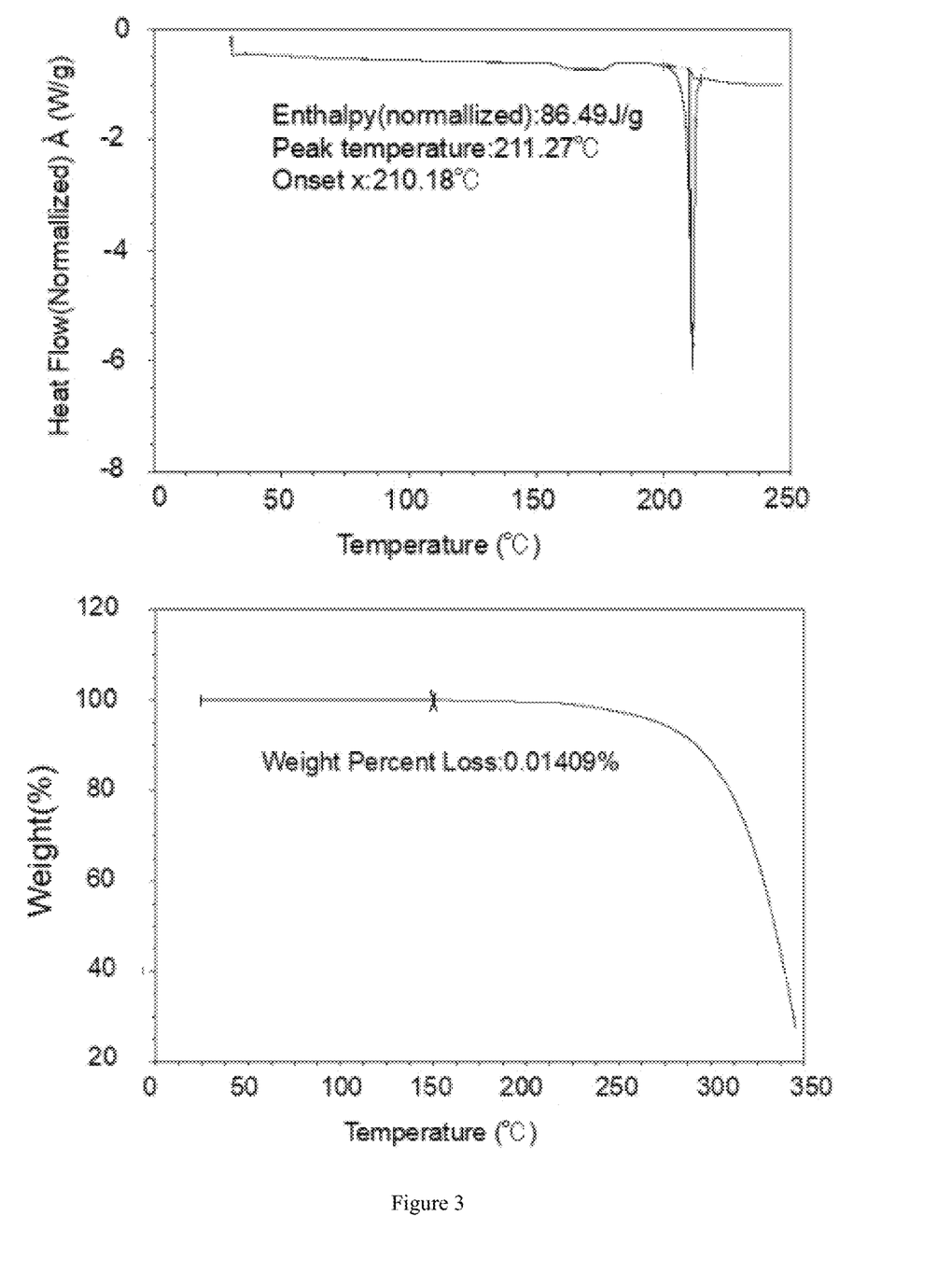
FIG. 3 shows DSC and TGA curves of crystal form A in embodiment 1 of the present invention.

The bulk pharmaceutical chemical is analyzed with X-ray diffractometer, and the results are shown in FIG. 2. It is observed that characteristic peaks appear at following 2-Theta angles, as listed in table 2. DSC and TGA curves of the bulk pharmaceutical chemical are shown in FIG. 3. It is determined that the crystal form of the bulk pharmaceutical chemical is crystal form A as described in WO20180399378.

TABLE 1

| Data of single crystal | | |
|---|---|---|
| Identification code | Form A | |
| Empirical formula | C25 H35 N3 O2 | |
| Formula weight | 409.56 | |
| Temperature | 273(2) K | |
| Wavelength | 1.54178 Å | |
| Crystal system | Monoclinic | |
| Space group | P2$_1$ | |
| Unit cell dimensions | a = 9.523(2) Å | □ = 90°. |
| | b = 9.923(2) Å | □ = 101.829(10)°. |
| | c = 12.157(2) Å | □ = 90°. |
| Volume | 1124.4(4) Å$^3$ | |
| Z | 2 | |

TABLE 2

| Characteristic peaks of the bulk pharmaceutical chemical | |
|---|---|
| 2-Theta | I % |
| 10.84 | 25.2 |
| 13.22 | 59.7 |
| 14.08 | 14.2 |
| 14.88 | 24.3 |
| 15.98 | 53.2 |
| 17.4 | 34.1 |
| 18.32 | 100 |
| 19.02 | 17.2 |
| 21.18 | 22 |
| 21.721 | 33.8 |
| 22.419 | 14.3 |
| 23.501 | 30.2 |
| 24.18 | 36 |
| 26.22 | 14.9 |
| 27.878 | 12.1 |

TABLE 2-continued

Characteristic peaks of the bulk pharmaceutical chemical

| 2-Theta | I % |
|---|---|
| 28.319 | 10.5 |
| 34.839 | 12.5 |

Figure 4:
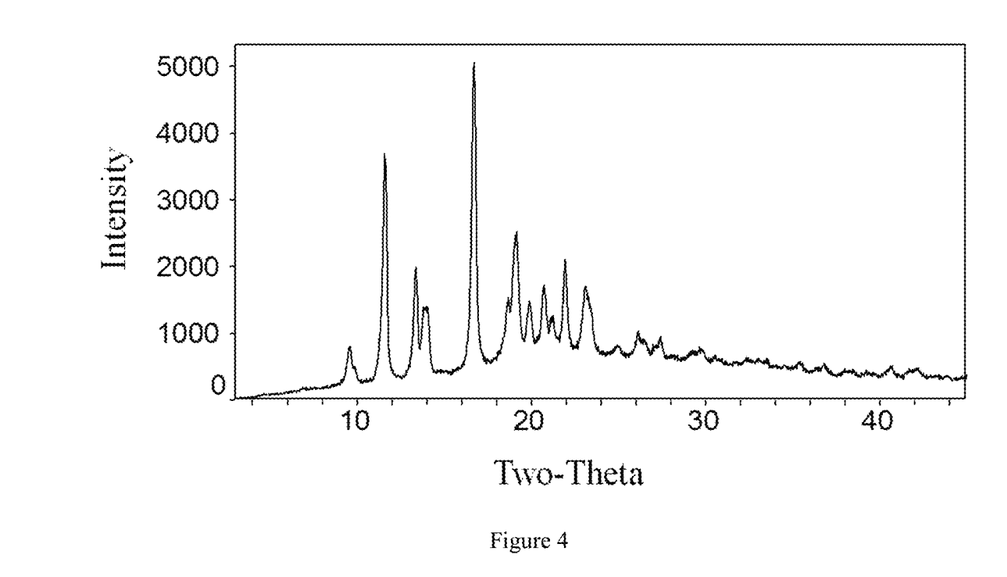
FIG. 4 shows a XRPD pattern of crystal form K in embodiment 2 of the present invention.

Example 2 Preparation of Crystal Form K 50.4 mg of bulk pharmaceutical chemical is heated to 180° C. at a heating rate of 10° C./min, then kept for 5 minutes, and cooled to room temperature at a rate of 10° C./min, thus obtaining a crystal form K. The XRPD pattern of crystal form K is shown in FIG. 4. It is observed that characteristic peaks appear at following 2-Theta positions.

TABLE 3

Characteristic peaks of crystal form K

| 2-Theta | I % |
|---|---|
| 9.561 | 16.1 |
| 11.581 | 75.7 |
| 13.38 | 40 |
| 14 | 31.8 |
| 16.719 | 100 |
| 18.661 | 22.1 |
| 19.159 | 54.7 |
| 19.881 | 10.6 |
| 20.739 | 16.2 |
| 21.941 | 20.9 |
| 23.1 | 35.1 |
| 26.156 | 10.1 |

Figure 5:
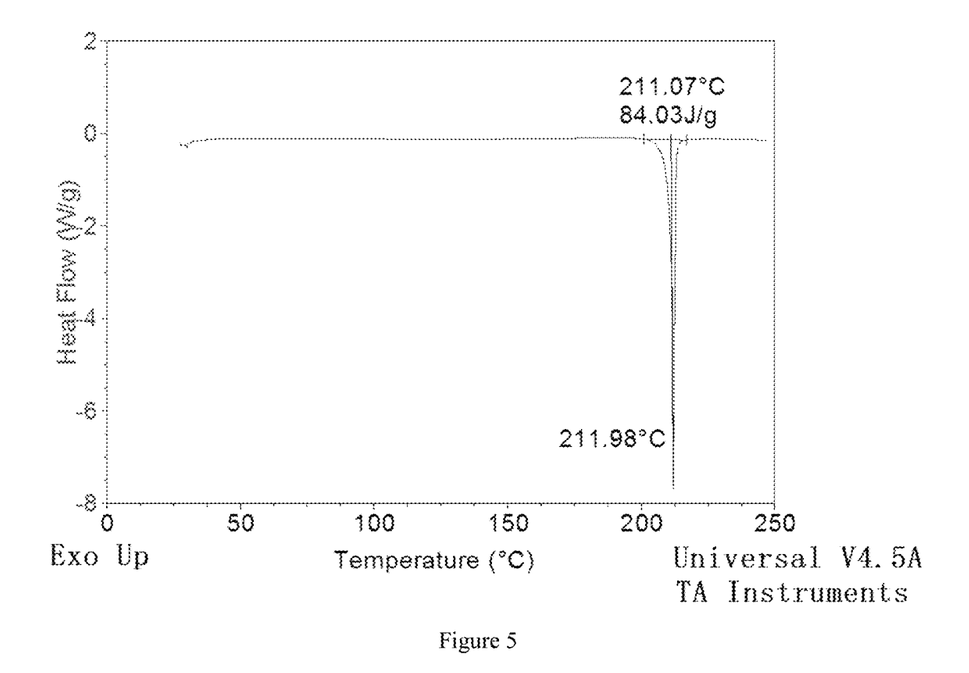
FIG. 5 shows a DSC curve of crystal form K in embodiment 2 of the present invention.
Figure 6:
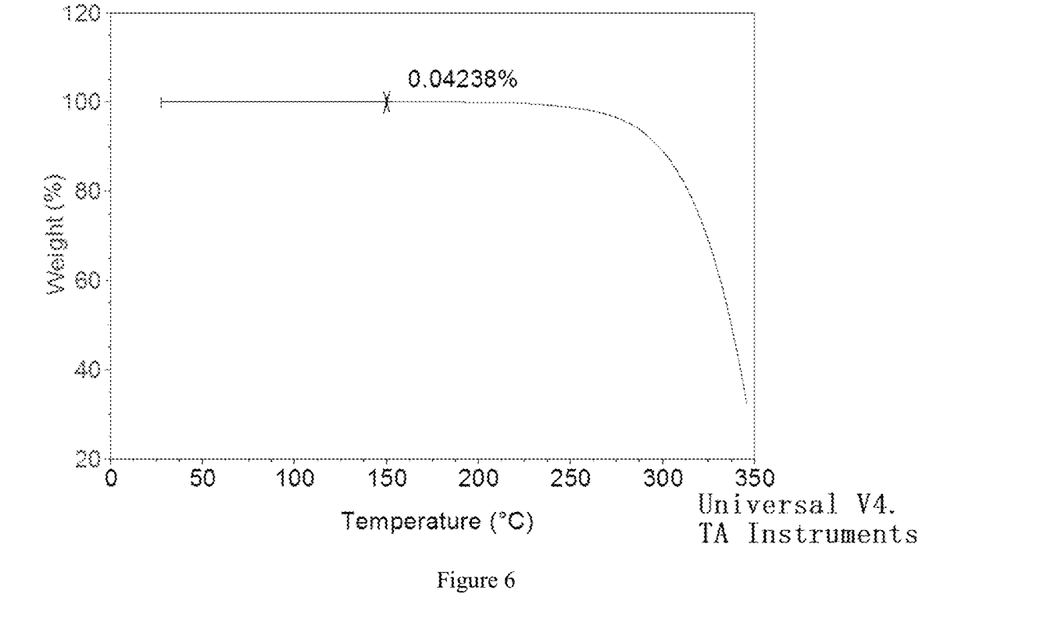
FIG. 6 shows a TGA curve of crystal form K in embodiment 2 of the present invention.

DSC and TGA characterizations are carried out for the obtained white solid, and the curves are shown in FIGS. 5 and 6. It is observed that, there is an absorption peak at 211.07° C. in the DSC curve, with a weight loss of 0.04% in the TGA curve. This weight loss indicates that the sample contains a very small amount of volatile substances (less than 0.1%), and indicates the crystal form K is not a hydrate or other solvates, and also indicates that the obtained solid has been fully dried.

Example 3 Preparation of Crystal Form K 44.9 mg of bulk pharmaceutical chemical is added into a sample vial, and dissolved with 1 mL of dichloromethane to produce a clear solution. The clear solution is allowed to undergo slow evaporation to obtain a solid. The solid is dried under vacuum at room temperature to obtain white powders. The white powders are dried in an oven at 100° C. for 0.5 hours to obtain a crystal form K. XRPD pattern of the crystal form K is found to be consistent with FIG. 4.

Example 4 Preparation of Crystal Form K 10.9 mg of the bulk pharmaceutical chemical is added into a sample vial, and dissolved with 0.06 mL of tetrahydrofuran to produce a clear solution. Then 0.2 mL of n-hexane is slowly added dropwise into the clear solution, and the clear solution turns to turbid. The turbid solution is filtered to obtain a solid. The solid is dried under vacuum to obtain white powders, and the white powders are dried in an oven at 100° C. for 0.5 h to obtain a crystal form K. XRPD pattern of the obtained crystal form K is consistent with FIG. 4.

Figure 8:
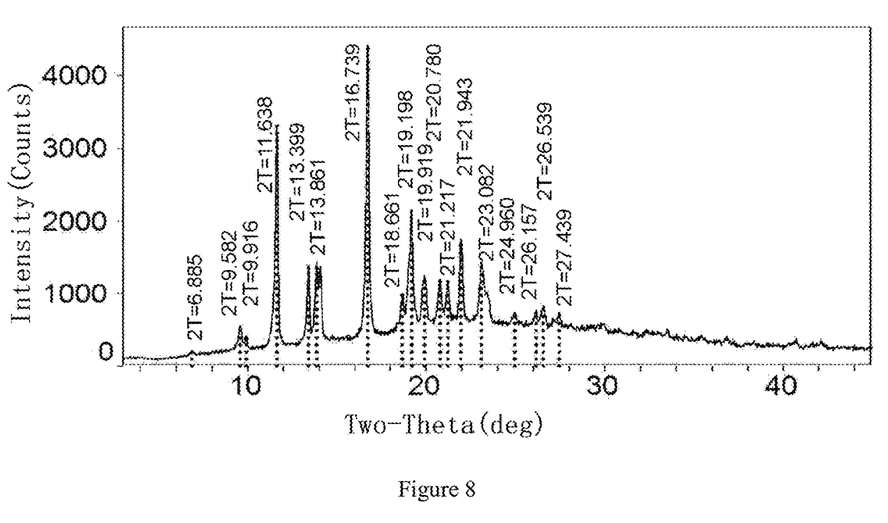
FIG. 8 shows an XRPD pattern of crystal form X in embodiment 5 of the present invention (peak positions are marked)

Example 5 Preparation of Crystal Form X 54.4 mg of crystal form K was added into a sample vial, and is suspended in 1 mL of water at 50° C. for 24 hours. The suspension is filtered and dried to obtain a white solid which is crystal form X. The XRPD pattern of the crystal form X is shown in FIGS. 7 and 8. It is observed that there are characteristic peaks at following 2-Theta positions.

TABLE 4

Characteristic peaks of crystal form X

| 2-Theta | I % |
|---|---|
| 6.885 | 1.7 |
| 9.582 | 10.5 |
| 9.916 | 5.2 |
| 11.638 | 72.9 |
| 13.399 | 26.1 |
| 13.861 | 54.3 |
| 16.739 | 100 |
| 18.661 | 17 |
| 19.198 | 49.9 |
| 19.919 | 18.4 |
| 20.78 | 14.9 |
| 21.217 | 12.9 |
| 21.943 | 24.4 |
| 23.082 | 38.7 |
| 23.437 | 20.2 |
| 24.96 | 5 |
| 26.157 | 7.9 |
| 26.539 | 8.7 |
| 27.439 | 7.7 |

DSC and TGA characterizations are carried out for the white solid and the curves are shown in FIGS. 9 and 10. It is observed that, there is an absorption peak at 212.87° C. in the DSC curve, with a weight loss of 0.03% in the TGA curve. This weight loss indicates that the sample contains a very small amount of volatile substances (less than 0.1%), and indicates the crystal form X is not a hydrate or other solvates, and also indicates that the obtained solid has been fully dried.

Figure 11:
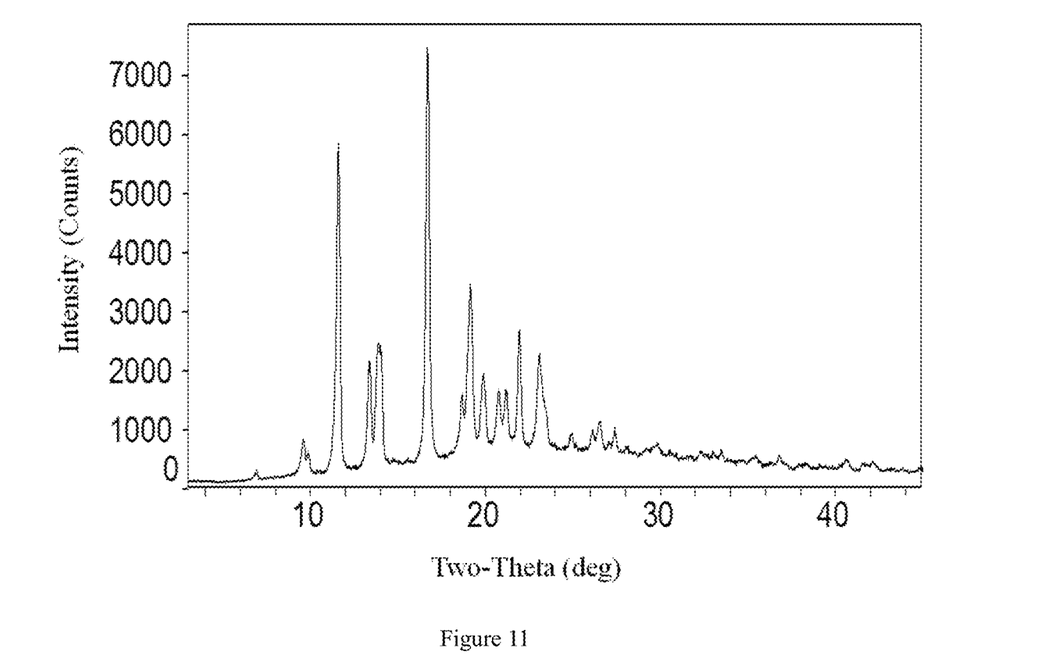
FIG. 11 shows an XRPD pattern of crystal form X in embodiment 6 of the present invention.

Example 6 Preparation of Crystal Form X 50.0 mg of crystal form K is added into a sample vial and placed at ambient conditions having a humidity of 92.5% RH and a temperature of 25° C. for 5 days, thus obtaining a white powder which is a crystal form X. XRPD pattern of this crystal form X is shown in FIG. 11.

Figure 12:
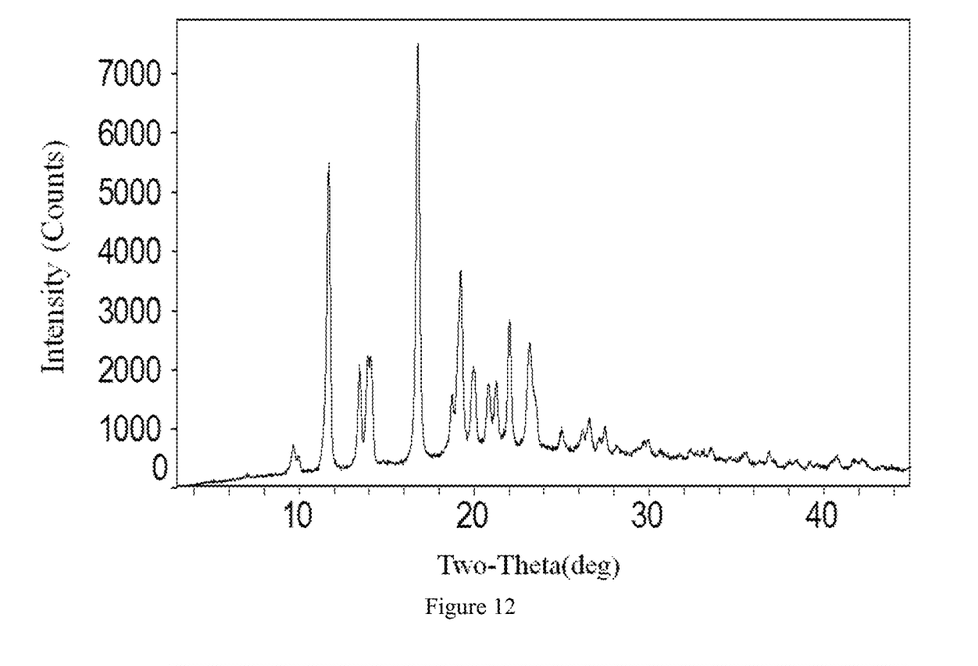
FIG. 12 shows an XRPD pattern of crystal form X in embodiment 7 of the present invention.

Example 7 Preparation of Crystal Form X 50.0 mg of crystal form K is added into a sample vial and placed at ambient conditions having a humidity of 75% RH and a temperature of 40° C. for 5 days, thus obtaining a white powder which is a crystal form X. XRPD pattern of this crystal form X is shown in FIG. 12. There are characteristic peaks at following 2-Theta positions.

Example 8 Preparation of Crystal Form X 40.2 mg of crystal form K is added into a sample vial, and suspended in 2 mL of water at 40° C. for 20 hours. Then the suspension is filtered and dried to obtain a white solid which is a crystal form X. XRPD pattern of this crystal form X is found to be consistent with FIG. 5.

Example 9 Preparation of Crystal Form X 59.6 mg of crystal form K is added into a sample vial, and suspended in 1 mL of water at 80° C. for 25 hours. Then the suspension is filtered and dried to obtain a white solid which is a crystal form X. XRPD pattern of this crystal form X is found to be consistent with FIG. 5.

Example 10 Preparation of Crystal Form X 50.0 mg of crystal form K is added into a sample vial and placed at ambient conditions having a humidity of 80% RH and a temperature of 35° C. for 7 days to obtain a white powder which is a crystal form X. XRPD pattern of this crystal form X is found to be consistent with FIG. 5.

Experimental Test Method

The crystal form X prepared in Example 5 is tested as follows.

Figure 13:
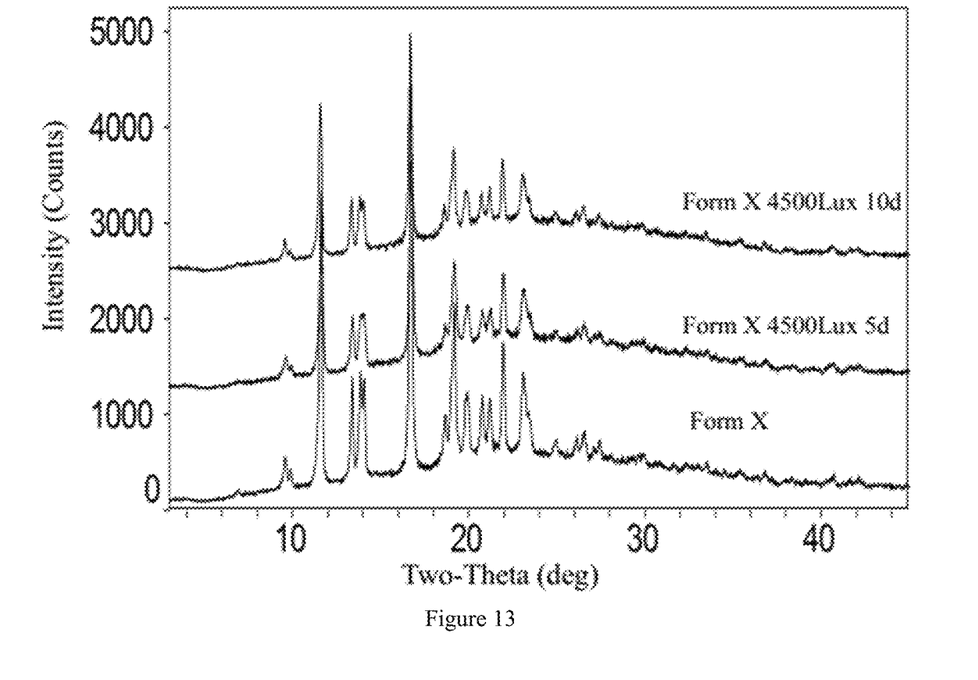
FIG. 13 shows comparison of XRPD patterns of crystal form X of the present invention to study stability under lights.

(1) Light stability: the test sample is placed in an environment having a temperature of 25° C. and a light condition of 4500 Lux for 5 days and 10 days, respectively, to test the stability of the crystal form. The results are shown in FIG. 13. The results show that the crystal form X has good light stability.

Figure 14:
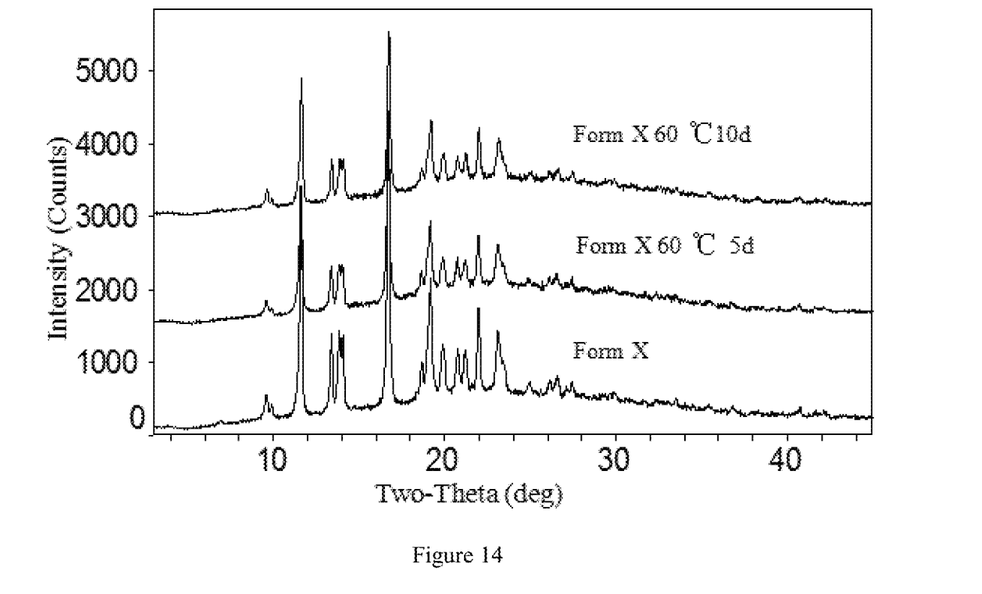
FIG. 14 shows comparison of XRPD patterns of crystal form X of the present invention to study stability under high temperatures.

(2) High-temperature stability: the test sample is placed at a temperature of 60° C. for 5 days and 10 days, respectively, to test the stability of the crystal form. The results are shown in FIG. 14. The results show that the crystal form X has good high-temperature stability.

Figure 15:
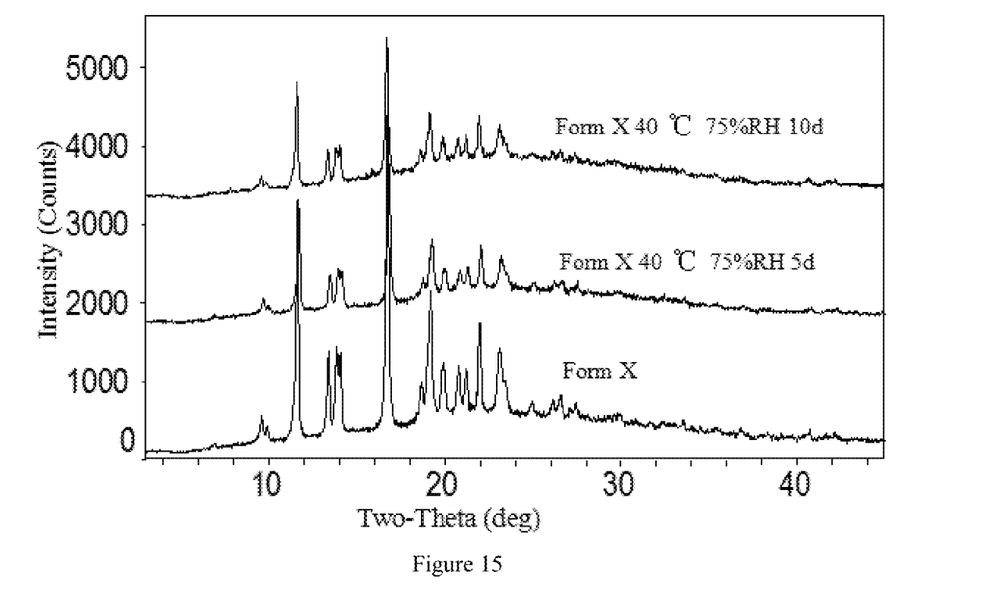
FIG. 15 shows comparison of XRPD patterns of crystal form X of the present invention to study accelerated stability.

(3) Accelerated stability: the test sample is placed in an environment having a humidity of 75% RH and a temperature of 40° C. for 5 days and 10 days, respectively, to test the stability of the crystal form. The results are shown in FIG. 15. The results show that the crystal form X has good accelerated stability.

Figure 16:
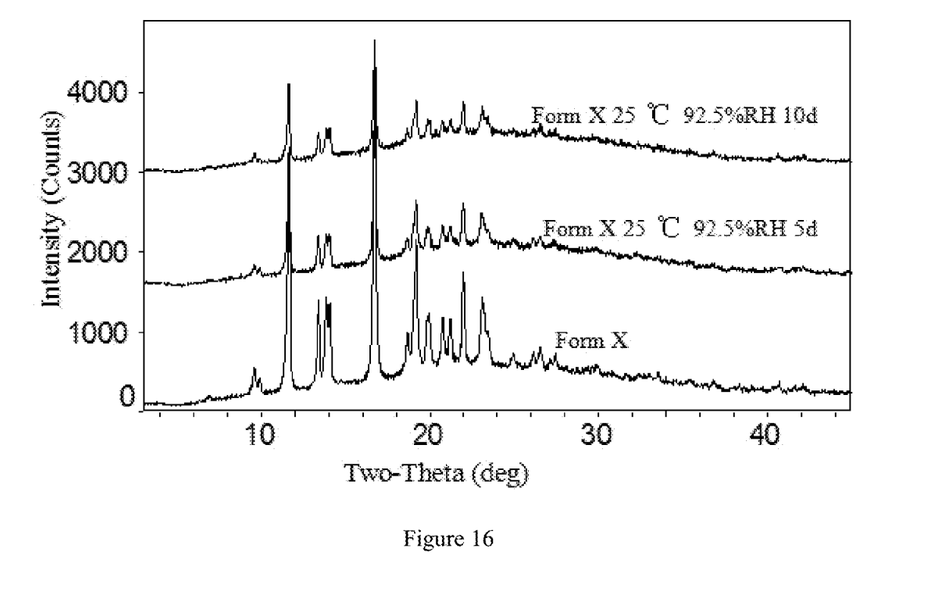
FIG. 16 shows comparison of XRPD patterns of crystal form X of the present invention to study stability under high humidity.

(4) High-humidity stability: the test sample is placed in an environment having a humidity of 92.5% RH and a temperature of 25° C. for 5 days and 10 days, respectively, to test the stability of the crystal form. The results are shown in FIG. 16. The results show that the crystal form X has good high-humidity stability.

Figure 17:
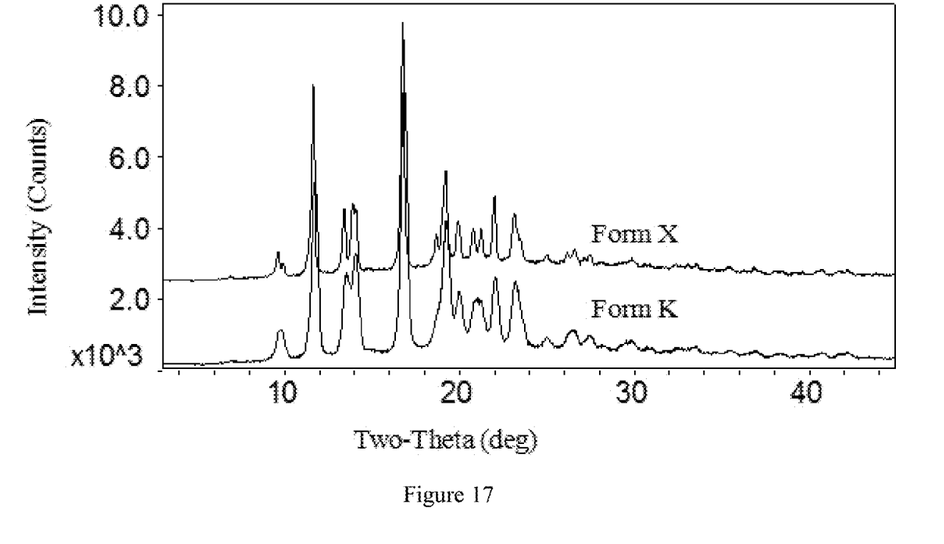
FIG. 17 shows comparison of XRPD patterns of crystal form X in embodiment 5 and crystal form K in embodiment 2 of the present invention.

In summary, crystal form X of 3α-hydroxy-3β-methyl-21-(4-cyano-1H-pyrazol-1'-yl)-19-nor-5β-pregnan-20-one provided in the present application has good light stability, high temperature stability, accelerated stability and high-humidity stability. As shown in FIG. 17, the crystal form X is different from crystal form K in the peak positions, peak shapes and relative intensities of characteristic peaks, and has better stability than the crystal form K.

Apparently, the aforementioned embodiments are merely examples illustrated for clearly describing the present invention, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. A crystal form X of γ-aminobutyric acid modulator, wherein, the γ-aminobutyric acid modulator is 3α-hydroxy-3β-methyl-21-(4-cyano-1H-pyrazol-1'-yl)-19-nor-5β-pregnan-20-one, and the crystal form X has characteristic peaks at 2θ diffraction angles of 9.582°±0.2°, 9.916°±0.2°, 11.638°±0.2°, 13.399°±0.2°, 13.861°±0.2°, 16.739°±0.2°, 18.661°±0.2°, 19.198°±0.2°, 19.919°±0.2°, 20.78°±0.2°, 21.217°±0.2°, 21.943°±0.2°, 23.082°±0.2° and 23.437°±0.2° in X-ray powder diffraction pattern.

2. The crystal form X of claim 1, wherein, the crystal form X has characteristic peaks at 2θ diffraction angles of 24.96°±0.2°, 26.157°±0.2°, 26.539°±0.2° and 27.439°±0.2° in X-ray powder diffraction pattern.

3. The crystal form X of claim 1, wherein, the crystal form X has following characteristic peaks in X-ray powder diffraction pattern:

| No. of Peaks | 2θ (°) | Relative intensity (%) |
| --- | --- | --- |
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |
| 13 | 23.082 | 38.7 |
| 14 | 23.437 | 20.2. |

4. The crystal form X of claim 1, wherein, the crystal form X has following characteristic peaks in X-ray powder diffraction pattern:

| No. of Peaks | 2θ (°) | Relative intensity (%) |
| --- | --- | --- |
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |
| 13 | 23.082 | 38.7 |
| 14 | 23.437 | 20.2 |
| 15 | 24.96 | 5 |
| 16 | 26.157 | 7.9 |
| 17 | 26.539 | 8.7 |
| 18 | 27.439 | 7.7. |

5. The crystal form X of claim 1, wherein, the crystal form X has a X-ray powder diffraction pattern as shown in FIG. 7.

6. The crystal form X of claim 1, wherein, the crystal form X has a characteristic absorption peak at 212.9±2° C. in differential scanning calorimetry curve.

7. The crystal form X of claim 1, wherein, the crystal form X has a differential scanning calorimetry curve as shown in FIG. 9.

8. The crystal form X of claim 1, wherein, the crystal form X has a weight loss of 0.03% before a temperature of 200° C. in thermal gravimetric analysis curve.

9. The crystal form X of claim 1, wherein, the crystal form X has a thermal gravimetric analysis curve as shown in FIG. 10.

10. A method for preparing the crystal form X of claim 1, comprising the following steps:

adding a proper amount of water into a crystal form K to suspend the crystal form K in water at a temperature of 40° C. to 80° C. for 20 h to 25 h to obtain a suspension, filtering the suspension and drying the filter cake to obtain a white solid which is a crystal form X.

11. The method of claim 10, wherein, a ratio of the crystal form K to water is (40 to 60)mg:(1 to 2) mL.

12. A method for preparing the crystal form X of claim 1, comprising the following steps:
placing a crystal form K in an environment having a humidity of 75% RH to 92.5% RH and a temperature of 25° C. to 40° C. for 3 days to 7 days to obtain a white powder which is a crystal form X.

13. A pharmaceutical composition, comprising the crystal form X of claim 1 and a pharmaceutically acceptable excipient.

14. A method for treating central nervous system diseases, comprising administering the crystal form X of claim 1 to a subject in need.

15. The method of claim 14, wherein, the central nervous system diseases is are selected from the group consisting of sleep disorder, mood disorder, schizophrenia spectrum disorder, spasticity disorder, memory disorder, cognitive disorder, dyskinesia, personality disorder, autism spectrum disorder, pain, traumatic brain injury, vascular disease, substance abuse disorder, withdrawal syndrome, or tinnitus, and any combination thereof.

16. The method of claim 14, wherein, the crystal form X is administered orally, parenterally, intradermally, intrathecally, intramuscularly, subcutaneously, vaginally, buccally, sublingually, rectally, topically, by inhalation, intranasally or transdermally.

17. A method for treating sleep disorder, mood disorder, schizophrenia spectrum disorder, spasticity disorder, memory disorder, cognitive disorder, dyskinesia, personality disorder, autism spectrum disorder, pain, traumatic brain injury, vascular disease, substance abuse disorder and/or withdrawal syndrome or tinnitus, comprising a step of administering a pharmaceutically effective amount of the pharmaceutical composition of claim 13 to a subject.

18. The crystal form X of claim 2, wherein, the crystal form X has following characteristic peaks in X-ray powder diffraction pattern:

| No. of Peaks | 2θ (°) | Relative intensity (%) |
| --- | --- | --- |
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |
| 13 | 23.082 | 38.7 |
| 14 | 23.437 | 20.2. |

19. The crystal form X of claim 2, wherein, the crystal form X has following characteristic peaks in X-ray powder diffraction pattern:

| No. of Peaks | 2θ (°) | Relative intensity (%) |
| --- | --- | --- |
| 1 | 9.582 | 10.5 |
| 2 | 9.916 | 5.2 |
| 3 | 11.638 | 72.9 |
| 4 | 13.399 | 26.1 |
| 5 | 13.861 | 54.3 |
| 6 | 16.739 | 100 |
| 7 | 18.661 | 17 |
| 8 | 19.198 | 49.9 |
| 9 | 19.919 | 18.4 |
| 10 | 20.78 | 14.9 |
| 11 | 21.217 | 12.9 |
| 12 | 21.943 | 24.4 |
| 13 | 23.082 | 38.7 |
| 14 | 23.437 | 20.2 |
| 15 | 24.96 | 5 |
| 16 | 26.157 | 7.9 |
| 17 | 26.539 | 8.7 |
| 18 | 27.439 | 7.7. |

20. The crystal form X of claim 2, wherein, the crystal form X has a X-ray powder diffraction pattern as shown in FIG. 7.

* * * * *